United States Patent [19]

Royster, Jr. et al.

[11] Patent Number: 5,866,314
[45] Date of Patent: Feb. 2, 1999

[54] PREPARATION AND USE OF A DIMETHYLAMINE SILVER CHLORO-IODIDE COMPLEX AS A SINGLE SOURCE PRECURSOR FOR IODIDE INCORPORATION OF SILVER CHLORIDE CRYSTALS

[75] Inventors: Tommie L. Royster, Jr.; Seshadri Jagannathan, both of Rochester; Jerzy A. Budz; Jerzy Z. Mydlarz, both of Fairport, all of N.Y.

[73] Assignee: Eastman Kodak Company, Rochester, N.Y.

[21] Appl. No.: 866,853

[22] Filed: May 30, 1997

[51] Int. Cl.$^6$ ............... G03C 1/005; C01G 5/00; C01G 5/02; C07F 1/10
[52] U.S. Cl. ............... 430/569; 423/23; 423/42; 117/938; 205/507; 556/110
[58] Field of Search .............. 430/569; 423/23, 423/42; 117/938; 205/507; 556/110

[56] References Cited

U.S. PATENT DOCUMENTS

| 3,883,355 | 5/1975 | Walworth | 430/569 |
|---|---|---|---|
| 3,941,600 | 3/1976 | Walworth | 430/569 |
| 4,153,462 | 5/1979 | Gerber et al. | 430/569 |
| 4,340,666 | 7/1982 | Walworth | 430/569 |
| 5,478,718 | 12/1995 | Verbeeck et al. | 430/569 |
| 5,541,051 | 7/1996 | Verbeeck et al. | 430/569 |
| 5,604,087 | 2/1997 | Lapp et al. | 430/569 |
| 5,759,762 | 6/1998 | Budz et al. | 430/611 |

OTHER PUBLICATIONS

Aldrich Catalog, p. 566, No. 12,636–5, Aldrich Chemical Company, Milwaukee, WI, 1996.

*Primary Examiner*—Mark F. Huff
*Attorney, Agent, or Firm*—Arthur H. Rosenstein

[57] ABSTRACT

A dimethylamine silver chloro-iodide complex is used as a single source precursor for iodide incorporation in silver chloride crystals.

8 Claims, No Drawings

5,866,314

PREPARATION AND USE OF A DIMETHYLAMINE SILVER CHLORO-IODIDE COMPLEX AS A SINGLE SOURCE PRECURSOR FOR IODIDE INCORPORATION OF SILVER CHLORIDE CRYSTALS

FIELD OF THE INVENTION

This invention relates to the process of iodide incorporation in silver chloride crystals. In particular, it relates to the use of a unique silver halide complex contained in a dimethylamine solution that can be used as single source material for the incorporation of iodide in silver chloride emulsions.

BACKGROUND OF THE INVENTION

Silver halide emulsions are generally prepared using a reactive precipitation process; aqueous solutions of silver nitrate and alkali halides are reacted in the presence of gelatin. The composition of resultant product (silver halide emulsions) is tuned by varying the constituents of the alkali halide solution. For example, the precipitation of pure silver bromide emulsions is carried out using sodium bromide as the alkali halide, while silver chloride emulsions are precipitated using sodium chloride as the alkali halide. Appropriate addenda/dopants are generally introduced as aqueous solutions during the precipitation process, to generate silver halide emulsions of desired composition.

The important feature of all these processes is the bimolecular chemical reaction between (Ag+) ions and the appropriate anion(s) to generate the precipitating species. It is possible to vary the chemical and the structural composition of the product emulsion by varying the constituents of the reagent solutions, but the chemical reaction responsible for the generation of the desired silver halide emulsion is always the reaction between (Ag+) ions that are present in a solution or on the surface of the silver halide emulsion, and the appropriate anion(s).

From an operational point of view, generation of silver halide emulsions by this reactive precipitation process involves the addition of concentrated reagent solutions into a reactor under vigorous mixing conditions. The goal of the mixing process is to minimize the volume of the reactor that is exposed to the unreacted reagent solutions. However, even under ideal mixing conditions, the volume of the reactor that is exposed to the unreacted reagents is finite and relatively large.

In order to understand the reasons for the exposure of the reactor contents to unreacted reagents it is necessary to examine the mechanism of the mixing process. Mixing in emulsion precipitation processes is achieved by means of a rapidly spinning rotary agitator. The momentum generated by the rotary agitator results in the circulation of the fluid in the reactor. Appropriate baffling devices are used to randomize the fluid motion in the reactor, to achieve efficient mixing. It is important to recognize that efficient mixing requires rapid circulation of the fluid in thereafter. In a typical emulsion generation process, the reagent solutions are introduced into a region of the reactor that experiences good mixing. Consequently, the concentrated reagent solutions are introduced into a region of the reactor that experiences rapid circulation of the fluid in the reactor; i.e. the reagent introduction region in the reactor is exposed frequently to the contents of the reactor.

It is also important to recognize that efficient mixing is necessary at the reagent introduction region, in order to promote the reaction between the concentrated reagents. Because this (efficient) mixing process is carried out by rapid circulation of the reactor fluid through the reagent introduction region, the contents of the reactor are necessarily exposed to the concentrated reagents. From a kinetic view point, the extent of exposure of the reactor contents to the unreacted reagents would depend on the rate of dilution of the concentrated reagents relative the rate of the chemical reaction between the concentrated reagents. Under ideal mixing conditions, the rate of dilution of the concentrated reagents is determined by the molecular/ionic diffusivity of the reactant species; which is still considerably smaller than the rate of the relevant chemical reactions. Hence, the extent of exposure of the reactor contents to the unreacted reagents can be significant even under ideal mixing conditions.

The unintentional exposure of the reactor contents to the unreacted reagents can have undesired effects on the emulsion crystals. For example, exposure of emulsion crystals to unreacted silver nitrate can result in the creation of fog centers in the crystals, while exposure of emulsion crystals to unreacted concentrated, potassium iodide can result in the destruction of grains. The grain destruction can be avoided by using dilute solutions of potassium iodide, solutions of iodide that also contain sodium bromide and long addition times. The disadvantages of this approach is the large volume of the reagents and the extension of the precipitation time (yield and productivity).

An alternative to the above approach is the use of silver iodide dissolved in an appropriate solvent as the source of iodide.

Halide introduction from concentrated solutions of silver halide complexes prepared from methylamineformamide and excess halide have been reported. However, methylamineformamide is exceedingly hazardous and the solvent has been documented as a teratosen (promotes deformity in embryos).

SUMMARY OF THE INVENTION

This invention addresses the limitations of the prior art for iodide incorporation in silver chloride crystals. A solution or low melting point solid of hydrated dimethylamine hydrochloride [$Me_2NH_2$]Cl) containing the silver iodide precursor complex [$Me_2NH_2$]$_n$[$AgICl_n$], is disclosed as a single source material for the incorporation of iodide into silver chloride crystals. Iodide incorporation is accomplished by introducing the precursor material to an aqueous medium of silver chloride crystals. Under aqueous conditions, iodide is released from the complex as silver iodide which eliminates the problems of free iodide supersaturation that results in destruction of silver chloride crystals. This process also provides kinetic control for releasing the silver iodide promoting homogeneous incorporation.

DETAILED DESCRIPTION OF THE PREFERRED EMBODIMENTS

This invention depends on the preparation of a silver chloro-iodide complex as a precursor to the formation of silver iodide for incorporation in silver chloride crystals. The complex [$Me_2NH_2$]$_n$[$AgICl_n$] contained in solid or liquid hydrated [$Me_2NH_2$]Cl provides a single source material for silver iodide precipitation. Preparation of the material can be accomplished by combining silver iodide with hydrated [$Me_2NH_2$]Cl or dissolving the isolated complex [$Me_2NH_2$][AgICl] in the hydrated salt.

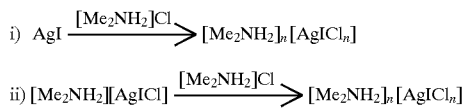

This invention uses the materials prepared by the above process to incorporate silver iodide into silver chloride crystals. Iodide incorporation is accomplished by introducing the hydrated $[Me_2NH_2]Cl$ that contains the precursor complex into an aqueous medium of silver chloride crystals.

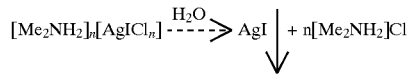

Thus, an amine salt $[(CH_3)_2NH_2]Cl$ can be hydrated with water and silver iodide can be introduced to form $[Me_2NH_2]_n[AgICl_n]$ or the amine salt can be combined with silver iodide in a dimethylformamide (DMF) solvent and heated to form crystals of the complex $[(CH_3)_2NH_2][AgICl]$ which are isolated and dissolved in hydrated $[Me_2NH_2]Cl$. Alternatively, concentrated HCl can be substituted for $[(CH_3)_2NH_2]Cl$ as the chloride source. The silver halide crystals involved are prepared using $[(CH_3)_2NH_2]_n[AgICl_n]$ as the source of iodide to form silver chloro-iodide crystals.

EXAMPLE 1

Method A

The amine salt $[Me_2NH_2]Cl$ was initially hydrated by using a stoichiometric amount of water (the water/amine mol ratio ranged from 1 –2). Then, silver iodide was introduced (the amine/silver mol ratio was $\leq 13$) followed by heating the mixture to steambath temperature. When a clear colorless solution was observed, the material was removed from the heat and allowed to cool to room temperature.

Method B

The amine salt $[Me_2NH_2]Cl$ was combined with silver iodide using a mol ratio of 1:1 in DMF solvent (an equivalent amount of concentrated HCl can be substituted for $[Me_2NH_2]Cl$). The mixture was then heated to steambath temperature until a clear colorless solution was observed. After cooling to room temperature, the solution was layered with diethyl ether and allowed to stand for 16 h. Crystals of the complex $[Me_2NH_2][AgICl]$ were isolated after decanting or filtering the solution followed by washing the material with diethyl ether. The isolated complex was then dissolved in the hydrated $[Me_2NH_2]Cl$ solvent.

The invention can be better appreciated by reference to the following Examples. Pure silver chloride emulsion was precipitated with the deposition of 0.2% of iodide with potassium iodide as a source of iodide at 92% into the grain formation and then pure chloride shell was deposited on the grains. This emulsion was designated as Emulsion A in Example 2. Emulsion B in Example 2 was prepared in an identical fashion, except that $[Me_2NH_2][AgICl]$ was used as the source of iodide.

EXAMPLE 2

Substrate

A reaction vessel contained 3.5 L of a solution that was 4.3% in gelatin, 21 grams in NaCl, 26 mg of glutarami- dophenyldisulfide (GdPD), and 0.25 mL of Nalco 2341 antifoaming agent. The contents of the reaction vessel were maintained at 68° C., and the pCl was adjusted to 1.0. To this stirred solution at 68° C. was added simultaneously and at 75 mL/min each 2.1M $AgNO_3$ and 2.5M NaCl solutions over 12.75 minutes. The NaCl solution contained an osmium dopant. Then these solutions were added at ramped flow from 75 to 142 mL/min over 30 minutes, followed by the addition of iridium dopant. Then the addition of silver and salt resumed for another 4.28 minutes. Finally the emulsion was cooled down to 43° C. over 8 minutes. The emulsion was then washed using an ultrafiltration unit, and its final pH and pCl were adjusted to 5.6 and 1.8, respectively. The resulting emulsion was a cubic grain silver chloride emulsion of 0.72 micron effective edge length size. This emulsion was used as the common substrate for the iodide incorporation in emulsions A and B.

Emulsion A

Approximately 3 moles of the substrate was redispersed in 7.5 kg of water containing ca. 80 g of sodium chloride water and heated to 70° C. with mixing. To this solution, 100 ml of a solution containing 1.1 g of potassium iodide and 30 g of sodium chloride was added by a rapid surface dump process and the mixture was held at 70° C. for 5 minutes with stirring. Subsequent to the hold period, a 4M solution of silver nitrate was added to the emulsion at a rate of 10 cc/min for 6.5 minutes. The final emulsion was cooled to 40° C., washed and concentrated to a final pH of 5.56 and pCl of 1.39, and characterized to have an effective cubic edge length of ca. 0.78 microns. The iodide content of the emulsion is calculated to be ca. 0.2%.

Emulsion B

This emulsion was prepared in the same manner as Emulsion A, with the following difference. The 100 ml of a solution containing 1.1 g of potassium iodide and 30 g of sodium chloride was replaced with 36.2 g of a hydrated $[Me_2NH_2]Cl$ solution of $[Me_2NH_2]_n[AgICl_n]$ with a AgI concentration of 0.18 mmol/g. The emulsion was washed and concentrated to a final pH of 5.58 and pCl of 1.48, characterized to have an effective cubic edge length of ca. 0.78 microns. The iodide content of this emulsion is also calculated to be ca. 0.2%.

EXAMPLE 3

Photographic Comparison of Emulsions A and B in Example 2 Sensitized Blue Light Exposure Emulsions A and B were sensitized as follows:

A portion of silver chloride emulsion was melted at 40° C. and the optimum amount of colloidal gold-sulfide and then a blue sensitizing dye were added. Then the emulsion was heated to 55° C. and ripened for 40 minutes. After cooling down to 40° C. 1-(3-acetomidophenyl)-5-mercaptotetrazole was added.

All emulsions were cooled at 26 mg silver per square foot on resin-coated paper support. The coatings were overcoated with gelatin layer and the entire coating was hardened with bis(vinylsulfonylmethyl)ether.

Coatings were exposed gradation exposure tablet with white light at 1/10 second and then processed in Kodak™ Ektacolor RA-4 processing. Photographic speed was measured at density=1.0. .

TABLE 1

Sensitometric Results

| Emulsion | Minimum Density | Maximum Density | Speed | Contrast |
|---|---|---|---|---|
| A-Blue | 0.072 | 2.93 | 115.8 | 2.76 |
| B-Blue | 0.069 | 2.92 | 128.3 | 3.33 |

EXAMPLE 4

Photographic Comparison of Emulsions A and B in Example 2 Sensitized for Green Light Exposures This example compares both emulsions sensitized for green light exposures.

Emulsions A and B were sensitized as follows:

A portion of silver chloride emulsion was melted at 40° C. with a green sensitizing dye and optimum amount of colloidal gold-sulfide. Then the emulsion was heated to 60° C. and ripened for 30 minutes. After cooling down to 40°C 1-(3-acetomidophenyl)-5-mercaptotetrazole was added followed by the addition of small amount of potassium bromide.

All emulsions were coated at 26 mg silver per square foot on resin-coated paper support. The coatings were overcoated with gelatin layer and the entire coating was hardened with bis(vinylsulfonylmethyl)ether.

Coatings were exposed gradation exposure tablet with white light at 1/10 second and then processed in Kodak™ Ektacolor Ra-4 processing. Photographic speed was measured at density=1.0..

TABLE 2

Sensitometric Results

| Emulsion | Minimum Density | Maximum Density | Speed | Contrast |
|---|---|---|---|---|
| A-Green | 0.200 | 2.31 | 238 | 2.20 |
| B-Green | 0.180 | 2.39 | 244 | 3.18 |

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

We claim:

1. A method of preparing a solution of a dimethylamine silver chloro-iodide complex $[(CH_3)_2NH_2]_n[AgICl_n]$ in water wherein n=1 to 4 comprising reacting AgI with $[(CH_3)_2NH_2]Cl$ and water.

2. The method of preparing and isolating $[(CH_3)_2NH_2][AgICl]$ comprising adding $[(CH_3)_2NH_2]Cl$ to AgI in the presence of dimethylformamide.

3. The method of preparing and isolating $[Me_2NH_2][AgICl]$ comprising adding concentrated HCl to AgI in the presence of dimethylformamide.

4. An isolated crystal of a complex having the structure: $[(CH_3)_2NH_2][AgICl]$.

5. The method of preparing a solution of a dimethylamine silver chloro-iodide complex $[(CH_3)_2NH_2]_n[AgICl_n]$ in water comprising dissolving $[(CH_3)_2NH_2][AgICl]$ in $[(CH_3)_2NH_2]Cl$ and water wherein n is 1 to 4.

6. A method of precipitating silver iodide comprising introducing a solution containing the single source precursor $[(CH_3)_2NH_2]_n[AgICl]_n$ in water wherein n is 1 to 4.

7. A method of incorporating iodide into silver chloride crystals comprising introducing $[(CH_3)_2NH_2]_n[AgICl_n]$ into a silver chloride emulsion wherein n is 1 to 4.

8. A method of incorporating iodide into silver chloro-iodide crystals comprising introducing $[(CH_3)_2NH_2]_n[AgICl_n]$ into a silver chloro-iodide emulsion wherein n is 1 to 4.

* * * * *